(12) United States Patent
Badger et al.

(10) Patent No.: US 8,538,129 B2
(45) Date of Patent: Sep. 17, 2013

(54) MASK PROGRAM DEFECT TEST (75) Inventors: Karen D. Badger, Milton, VT (US); Emily E Gallagher, Burlington, VT (US); Christoper Magg, Essex Junction, VT (US)

(73) Assignee: International Business Machines Corporation, Armonk, NY (US)

( * ) Notice: Subject to any disclaimer, the term of this patent is extended or adjusted under 35 U.S.C. 154(b) by 762 days.

(21) Appl. No.: 12/576,597

(22) Filed: Oct. 9, 2009

(65) Prior Publication Data

US 2011/0085723 A1    Apr. 14, 2011

(51) Int. Cl.
*G06K 9/00* (2006.01)

(52) U.S. Cl.
USPC ........................................... 382/144

(58) Field of Classification Search
USPC ................................. 382/141, 144
See application file for complete search history.

(56) References Cited

U.S. PATENT DOCUMENTS

| | | | | |
|---|---|---|---|---|
| 4,809,341 | A | * | 2/1989 | Matsui et al. ............... 382/144 |
| 6,282,309 | B1 | | 8/2001 | Emery |
| 6,482,557 | B1 | * | 11/2002 | Chen et al. ................... 430/30 |
| 6,721,695 | B1 | * | 4/2004 | Chen et al. ..................... 703/7 |
| 6,873,720 | B2 | * | 3/2005 | Cai et al. .................... 382/149 |
| 7,254,251 | B2 | * | 8/2007 | Cai et al. .................... 382/100 |
| 7,403,649 | B2 | * | 7/2008 | Cai et al. .................... 382/141 |
| 7,565,001 | B2 | * | 7/2009 | Cai et al. .................... 382/141 |
| 7,835,565 | B2 | * | 11/2010 | Cai et al. .................... 382/144 |
| 7,865,866 | B2 | * | 1/2011 | Kim et al. ..................... 716/50 |
| 8,121,393 | B2 | * | 2/2012 | Satou et al. ................. 382/144 |
| 2002/0164065 | A1 | * | 11/2002 | Cai et al. .................... 382/149 |
| 2008/0020298 | A1 | * | 1/2008 | Nagamura et al. ............ 430/5 |
| 2008/0205743 | A1 | * | 8/2008 | Huang et al. ............... 382/144 |
| 2008/0288912 | A1 | * | 11/2008 | Kim et al. ..................... 716/19 |
| 2009/0180680 | A1 | * | 7/2009 | Satou et al. ................. 382/144 |
| 2011/0116085 | A1 | * | 5/2011 | Lim et al. .................. 356/237.5 |

* cited by examiner

*Primary Examiner* — Roy M Punnoose
(74) *Attorney, Agent, or Firm* — Richard M. Kotulak (57) ABSTRACT

A method for characterizing the resolution of mask inspection tool using a test mask and a database containing defect data. A variety of defect types and sizes is programmed into the database, and the database is then used to inspect the defect-free mask. All defects programmed into the database are not captured in performing the method, so the resolution capability of an inspection tool can be determined.

12 Claims, 10 Drawing Sheets

Streamlined Invention Defect Test Mask Process

Figure 1. Current Programmed Defect Test Mask Process

Prior Art

Figure 2. Poorly resolved defects on programmed defect test masks

Figure 3. Streamlined Invention Defect Test Mask Process

Figure 4. Data0 - Representative data from a typical mask design

Figure 5. Mask0 is built from Data0 with normal processing and no defects.

Figure 6. Programmed defects are added to Data0 and relabeled as Data1

Figure 7a. Examples of typical programmed defect types on a line/space design

Figure 7b. Examples of typical programmed defect types on a hole design

Figure 8. Data1 is used to inpect Mask0. Differences between Data1 and Mask0 are highlighted by inspection tool as defects.

Figure 9. Example of a typical programmed defect test mask sensitivity chart

MASK PROGRAM DEFECT TEST

BACKGROUND OF THE INVENTION

1. Field of the Invention

This invention relates to the field of mask defect inspection. More specifically, characterizing defect detection sensitivity on inspection tooling.

2. Background of the Invention

In order to use an inspection tool effectively, its ability to detect defects or sensitivity must quantified. The threshold for detecting defects can vary from tool to tool and pattern to pattern. The standard method for assessing an inspection tool's sensitivity is to select relevant base mask patterns, insert programmed defects of many types and sizes, and then build the mask and inspect it on the inspection tool under test. The tool must be thoroughly characterized against a set of appropriate programmed defects, on mask designs that both challenge the inspection tool and are representative of the product that will be inspected on that tool. Test masks that are currently available consist of simple defect types programmed into simple background patterns, and seldom challenge the abilities of the mask inspection systems and may not be relevant to a specific customer.

It is important to understand the current practice of defect test mask generation. Mask are built with defects programmed into a base design. With the current method of building defect test masks, defects may be sized, for example, from 5 nm to 100 nm in 5 nm increments. The sizing of these defects on the final mask is difficult to predict and may not even resolve. Those that do resolve may have large gaps in size from row to row. Let us assume that an inspection tool sensitivity of 40 nm is needed. If the tool detects a 50 nm defect 100% of the time, but the next smallest defect is 25 nm, and it is only captured 60% of the time, the true capability of the tool is somewhere between 50 and 25 nm. This is not enough granularity to guarantee a 40 nm defect sensitivity.

Defects that resolve on the masks are then measured to determine sizing since there is not a one-to-one correspondence between design and printed defect. Multiple inspections from multiple inspection tools are used to calculate the probability of detection by defect size and type. Purchase specifications and defect sensitivity commitments are then interpolated from those results. Those commitments are based on how well defect types print and measure on a variety of test masks rather than how capable the inspection tool is. This mismatch in commitment versus actual capability is largely based on the quality and size of the defects which resolve on test masks.

In addition, the defect capability must be determined on multiple mask material types. This either multiplies the work or dictates that only a subset of masks will be used to represent the entire population of mask types.

Current test mask practices yields specifications that are tied to one or more physical test masks rather than to actual tool capability. The result is that the commitments are conservative and the test masks themselves become a portion of the specification of a tool. This creates risk for both the tool owner and the inspection tool supplier.

BRIEF SUMMARY OF THE INVENTION

This invention provides a method for designing and building programmed defect test masks that is independent of process resolution, defect measurement techniques, or mask material type.

Current test mask practices compare a 'defective' mask to a defect-free database. This invention uses a defect free mask that is compared to a 'defective' database. A variety of defect types and sizes is easily designed into the database that is used to inspect the defect-free mask. The resolution and size of these defects in the database is constant and is not dependent on process resolution or measurement variability. All defects programmed into the database remain, regardless of size so that a true resolution can be determined.

Repeatable and consistent results are achievable without investing valuable resources to build and measure a programmed test mask. The time lost by iterative defect sizing is eliminated. This is done if resolution assumptions are incorrect or if requirements change. In addition, test mask damage would no longer influence inspection tool performance commitments.

DETAILED DESCRIPTION OF THE INVENTION

Figure 1:
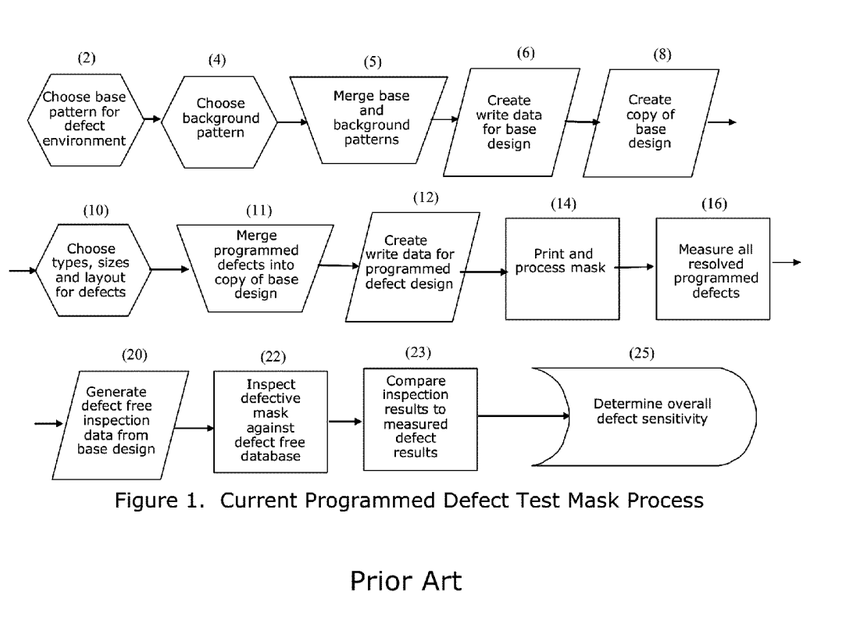
FIG. 1—Current defect test mask process

Current test mask generation involves a series of steps. These steps are illustrated in FIG. 1. The selection of base patterns is first. The base pattern 2 and any background patterns 4 are then merged as shown in 5. Then write data 6 and a copy of the base design 8 are created. The programmed defect types and defect size ranges are chosen as shown in 10 and then merged at 11 into the copy of the base design. Defects are placed within the base pattern and write-ready data is generated at 12. At 14 the mask is built using the desired substrate and process. All of the defects that resolved on the mask must be measured 16. From the base design, defect-free inspection data is generated 20 and used to inspect the defective mask 22. The inspection results are compared with the measured defect results to determine the minimum detectable defect type by size 23. From this process the defect sensitivity can be determined 25.

Figure 2:
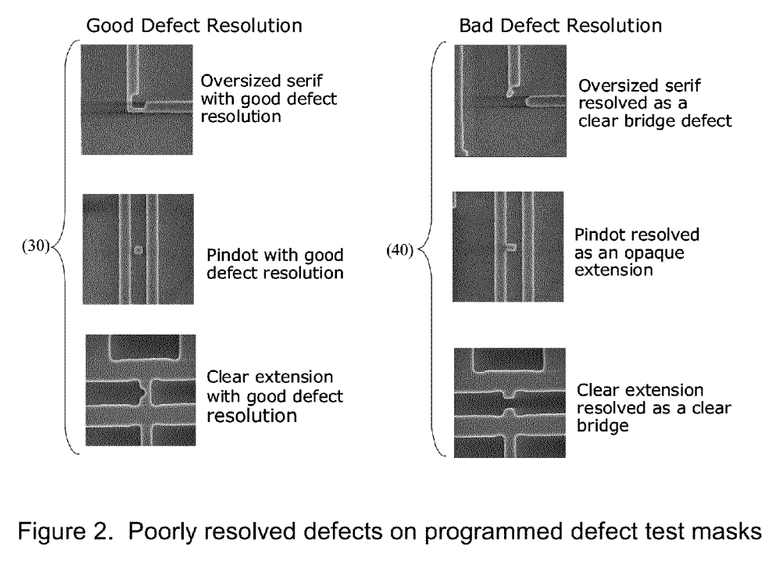
FIG. 2—Poorly-resolved defects on programmed defect test masks

This process must be repeated for major design types (i.e., lines/spaces versus hole layer designs), for each attenuator type and for each technology node. If sufficient quantity and sizes of defects do not resolve on the test mask, bias compensation must be added to the programmed defects in the design data and the process of building the test mask must be repeated. See FIG. 2 for examples of good defect resolution 30 and of defects that have not resolved well 40 on test masks. This process consumes considerable time (both human and tooling) and materials.

In contrast, this invention describes a process for adding programmed defects to the database rather than the mask. This eliminates the defect resolution variable and measurement requirement on the actual test mask. See FIG. 3 for the streamlined flow chart of the invention.

Figure 3:
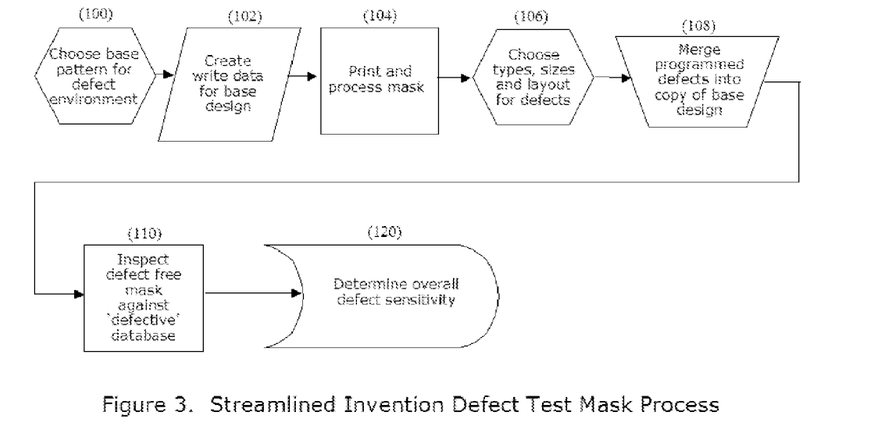
FIG. 3—Streamlined Invention Programmed Defect Test Mask Process
Figure 4:
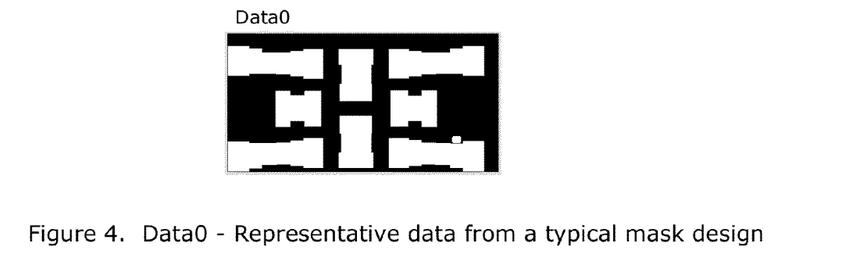
FIG. 4—Data0: representative data from a typical mask design

Step 1 of the process involves choosing a base pattern for the test mask at 100. This base pattern can be a sampling of images from an existing mask design. This base pattern will be denoted as Data0. See FIG. 4 for an example of representative data from a mask design. Write-ready data is prepared from this base design at 102.

Figure 5:
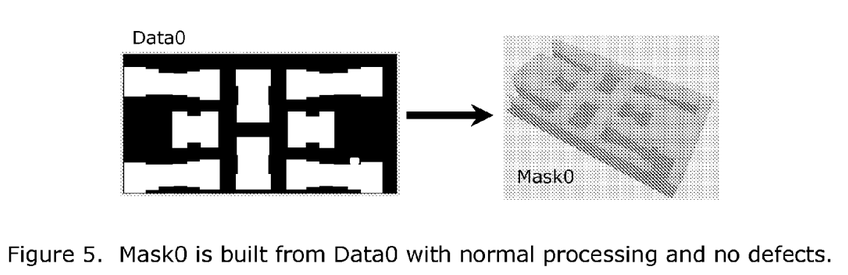
FIG. 5—Mask0: built from Data0 with normal processing and no defects

Next, at 104 a mask is printed from Data0. This mask is denoted Mask0. FIG. 5 illustrates a representative mask manufacture from Data0. Mask0 is a direct copy of Data0 and does not contain programmed defects.

Figure 6:
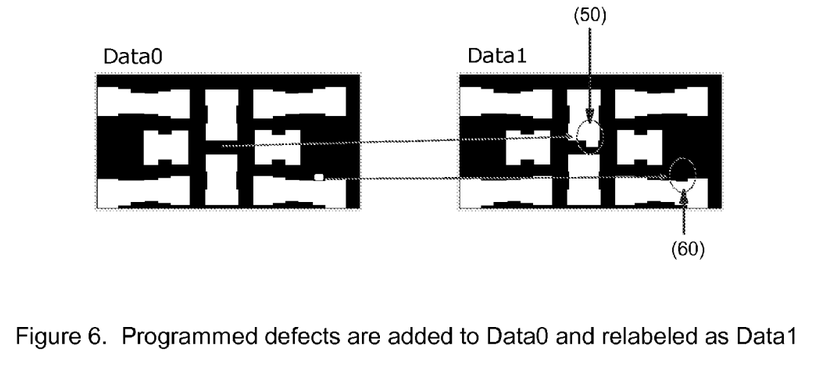
FIG. 6—Programmed defects are added to Data0 and relabeled as Data1
Figure 7A:
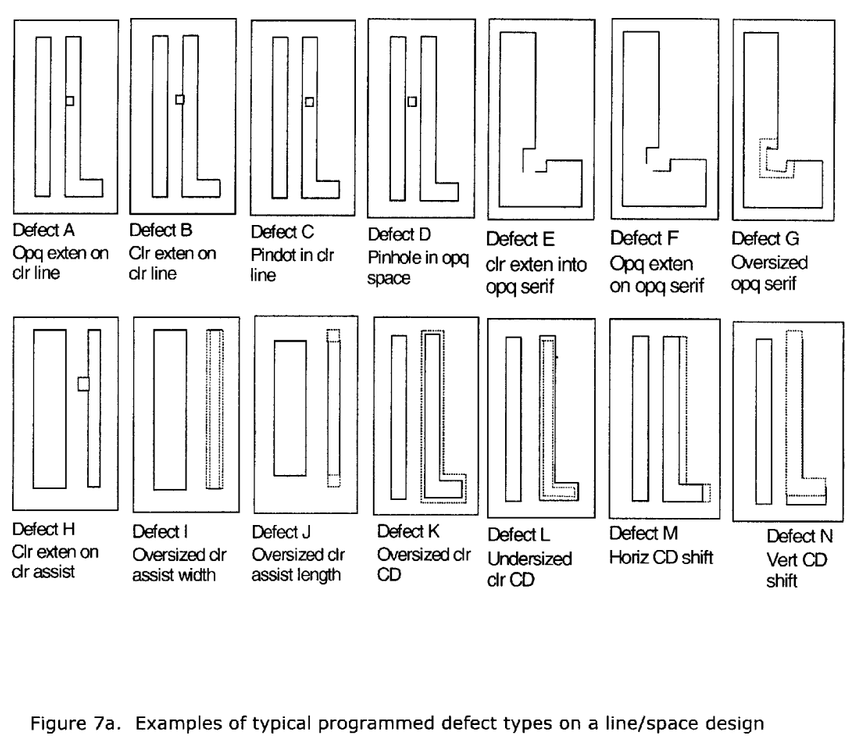
FIG. 7a—Typical programmed defect types on a line/space design
Figure 7B:
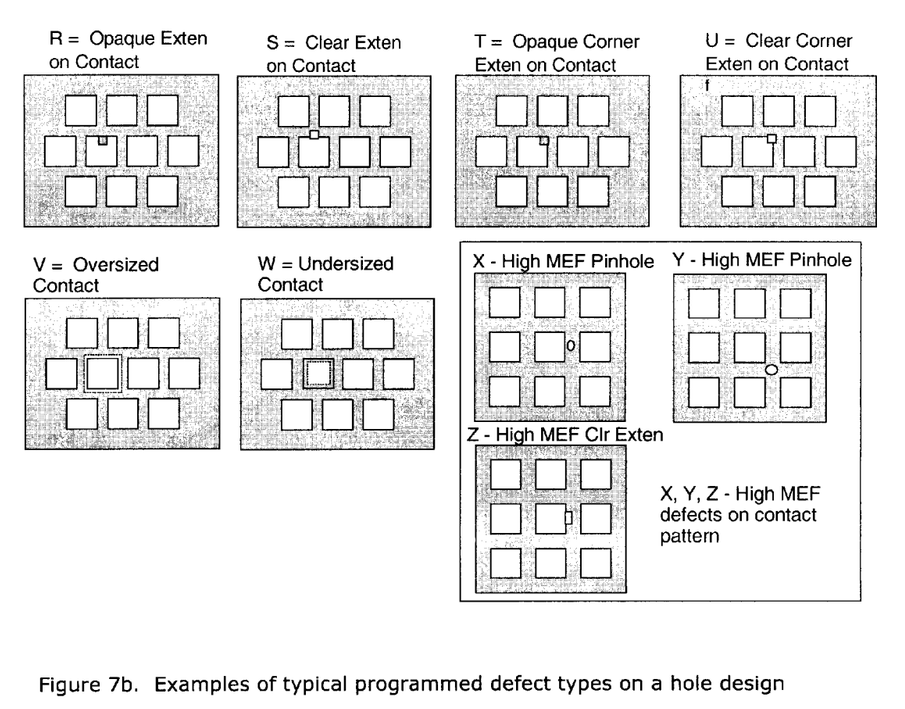
FIG. 7b—Typical programmed defect types on a hole layer design

A copy of Data0 is then created and denoted Data1 (108). At 106 programmed defects are chosen and merged into Data1 at 108. FIG. 6 depicts an example whereby two defects, 50 and 60, are added to the copy of Data0 now relabeled as Data1. Defects contained within Data1 include multiple defect types and a range of sizes for each type. These defects are placed systematically for ease of analysis. FIGS. 7a and 7b are illustrative examples of defect types.

Figure 8:
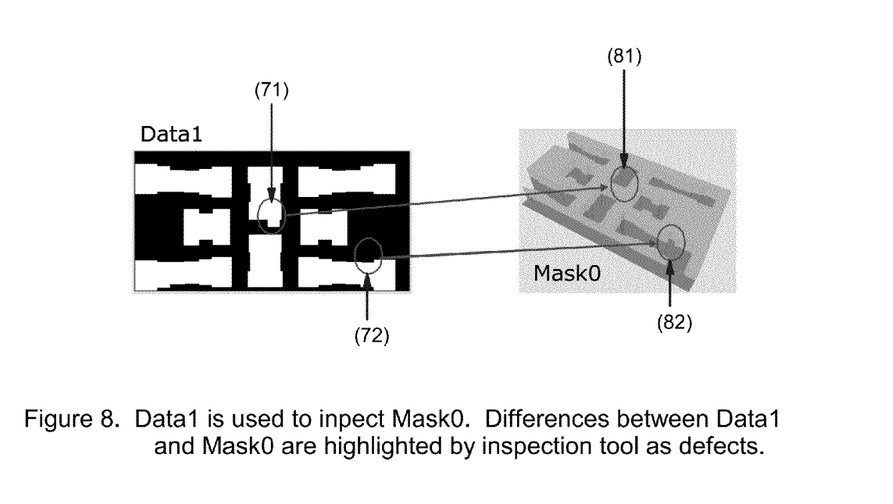
FIG. 8—Data1 is used to inspect Mask0

Mask0 is then inspected (a process 110 that compares the mask to reference data) using Data1 (with programmed defects) as reference data. This inspection identifies the differences between Mask0 and Data1. FIG. 8 is a simple example where programmed defects 71 and 72 are highlighted in the inspection of Mask0 as defects at locations 81 and 82.

Figure 9:
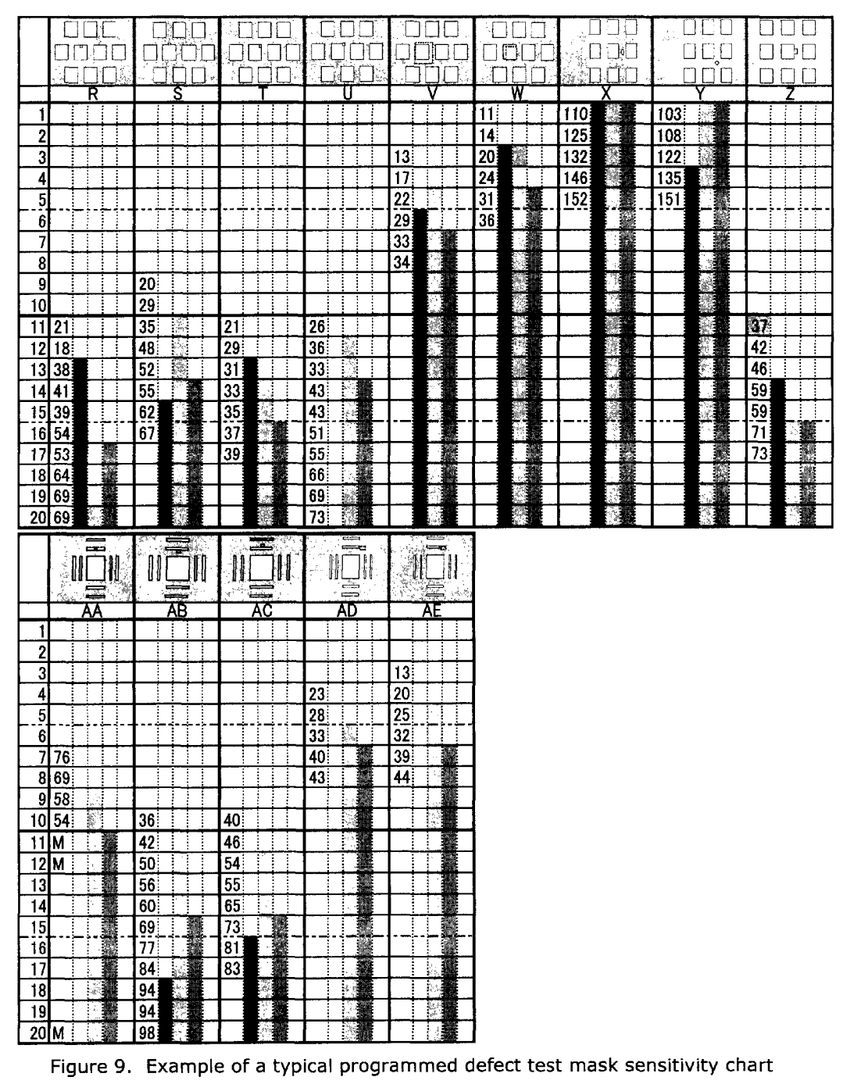
FIG. 9—Example of a typical programmed defect test mask sensitivity chart

Defects detected and not detected 120 define the capability of the mask inspection system. FIG. 9 is an example of a typical programmed defect test mask sensitivity chart. Sensitivity to defects on hole features is shown in the upper portion of the chart, R through Z. Sensitivity to defects on line features is shown in the lower portion AA-AE. Each bar represents sensitivity at different inspection conditions. Each numbered row (1 to 20) in a lettered group is a different defect size of the same type. The smaller the number, the smaller the defect size. If a cell is shaded, there is a 100% capture rate of that defect by the inspection tool. Higher bars indicate better sensitivity since the smaller defects are located near the top of the chart.

There are a number of advantages to using this process over the previous process.

1) Any mask can become a sensitivity mask
2) Defect sizes and locations can be easily modified at low risk and low cost
3) Cycles of learning are Increased because the time to generate a test mask is shortened and any given design can be much more flexible.
4) New mask designs can be quickly converted to sensitivity masks without a long build cycle.
5) The need to build and characterize individual programmed defect test masks is eliminated.
6) The same programmed defect data can be applied to multiple attenuator types or mask process flows without having to characterize individual test masks for each attenuator.

Today, if a test mask is damaged issues arise. Test masks must be rebuilt and totally characterized prior to use to include multiple inspections as well as CD and defect measurements and possibly AIMS measurements. This is a very costly and time-consuming process. A complication is that inspection tools are currently purchased against a hard programmed defect test mask, so there is reluctance on the equipment supplier's part to allow replacement of that mask without extensive correlation back to the original mask. This new approach would characterize tool performance against the defects in the database rather than on the mask. Since there are no concerns about resolution or size repeatability within the database, it makes characterization of replacement test masks unnecessary.

Allows for smaller and more repeatable increments in defect size 9.

Characterization of mask inspection tool is not dependent on quality of test mask. This provides one with the ability to accurately resolve 'programmed defects' on test mask (this allows a wider range of programmed defect sizes without fear of 'non-resolution' on the printed mask) or tooling specs being based on averaging of multiple same-model inspection tool performance.

There are also a number of other applications that this invention enables.

This invention can be integrated with optical proximity correction (OPC)/optical rules checking (ORC) or, more generically, OPC verification This invention could easily deploy mask defect analysis on defect location and sizing from lithography simulation hotspots generated by ORC, allows for verification of defects on new or modified OPC, and allows for easy characterization of defect types and sizes on next generation lithography approaches.

Today, product defect specifications are quantified by percentage of nominal CD and/or inspection tool capability. This invention permits defect specification to move to a metric that really matters, product defect printability. This will result in some defect specifications being tighten and other loosened, but in all cases, the quality of the inspection will be linked more tightly to the mask being inspected. This invention will also allow for the determination of printable defect types and sizes through simulation without having to build masks and can be used with AIMS and/or inspection tool simulation software/hardware This invention will also allow for quick redesigns of programmed defects to include additional defect types and size ranges without having to rebuild and re-characterize the test mask. It also aids in determining which types of defects are critical by pattern type rather than assuming all defect types apply equally to all masks.

The invention claimed is:

1. A method of characterizing an inspection apparatus by inspecting a patterned mask comprising:
   inspecting the patterned mask using a modified version of the base design comprising defect data, the mask produced from a base design and having a plurality of patterns which pass an inspection by the inspection apparatus;
   comparing the detected defects found by the inspection apparatus against the modified version of the base design.

2. The method of claim 1 where the modified version of the base design includes programmed defects which are outside the resolution capability of the inspection apparatus.

3. The method of claim 1 the defect data includes sizing defects.

4. The method of claim 1 where the patterns are of different feature types.

5. The method of claim 1 where the patterns are of different layouts.

6. The method of claim 1 also comprising printing and processing the mask.

7. The method of claim 2 also comprising merging the programmed defects into a copy of the base design.

8. The method of claim 2 also comprising determining the resolution sensitivity for the inspection apparatus by identifying which programmed defects were detected by the inspection apparatus.

9. The method of claim 4 where the programmed defect types are lines and spaces.

10. The method of claim 4 where the programmed defect types are holes.

11. A method of determining the resolution capability of an inspection apparatus for various patterns on a mask comprising:

inspecting the patterned mask using a modified version of the base design comprising programmed defect data, the mask produced from a base design and having a plurality of patterns which pass an inspection by an inspection apparatus; comparing the detected defects found by the inspection apparatus against the modified version of the base design; and identifying which programmed defects were detected by the inspection apparatus.

12. The method of claim 11 also comprising the step of comparing the identified programmed defects to a sensitivity chart.

* * * * *